(12) United States Patent
Utas et al.

(10) Patent No.: US 8,747,882 B2
(45) Date of Patent: Jun. 10, 2014

(54) CATHETER ASSEMBLY WITH BACTERICIDAL EFFECT

(75) Inventors: Jan Utas, Kungsbacka (SE); Andrea Schmid, Mölnlycke (SE); Agneta Nordholm, Mölndal (SE); Martin Nyman, Mölndal (SE)

(73) Assignee: Astra Tech AB, Molndal (SE)

( * ) Notice: Subject to any disclaimer, the term of this patent is extended or adjusted under 35 U.S.C. 154(b) by 1618 days.

(21) Appl. No.: 11/407,206

(22) Filed: Apr. 20, 2006

(65) Prior Publication Data

US 2006/0240069 A1 Oct. 26, 2006

(30) Foreign Application Priority Data

Apr. 21, 2005 (SE) ........................................ 0500890

(51) Int. Cl.
*A61L 29/14* (2006.01)

(52) U.S. Cl.
USPC ............ 424/423; 514/574; 514/568; 427/2.1

(58) Field of Classification Search
None
See application file for complete search history.

(56) References Cited

U.S. PATENT DOCUMENTS

| 4,489,097 | A | | 12/1984 | Stone | |
|---|---|---|---|---|---|
| 4,906,237 | A | * | 3/1990 | Johansson et al. | 604/265 |
| 5,800,412 | A | * | 9/1998 | Zhang et al. | 604/523 |
| 6,409,717 | B1 | * | 6/2002 | Israelsson et al. | 604/544 |
| 2003/0139730 | A1 | | 7/2003 | Bracken et al. | |
| 2004/0086722 | A1 | | 5/2004 | Madsen | |
| 2004/0091428 | A1 | * | 5/2004 | Libin | 424/49 |
| 2005/0043715 | A1 | * | 2/2005 | Nestenborg et al. | 604/544 |

FOREIGN PATENT DOCUMENTS

| EP | 0 647 452 A1 | 4/1994 |
|---|---|---|
| EP | 1 245 247 A1 | 10/2002 |
| GB | 1 582 992 | 1/1981 |
| GB | 2 353 936 A | 3/2001 |
| WO | WO-01/53414 A1 | 7/2001 |
| WO | WO-2004/030715 A1 | 4/2004 |
| WO | WO-2004/075944 A2 | 9/2004 |
| WO | WO-2005/061035 A1 | 7/2005 |
| WO | WO-2006/081392 A1 | 8/2006 |

OTHER PUBLICATIONS

Dawson et al, 1986. Data for Biochemical Research. Chapter 18. pH, buffers, and physiological media. p. 428.*
Waller et al, 1997. The importance of osmolality in hydrophilic urethral catheters: a crossover study. Spinal Cord, vol. 35:229-233.*
Cruess and Richert, 1929. Effect of hydrogen ion concentration on the toxicity of sodium benzoate to microorganisms. Journal of Bacteriology, vol. 5:363-371.*
Cruess et al "Effect of Hydrogen Ion Concentration on the Toxicity of Sodium Benzoate to Microorganisms," Journal of Bacteriology, vol. 5:363-371, 1929.*
Dawson et al Data for Biochemical Research. Chapter 18. pH, buffers, and physiological media, p. 428, 1986.*
Rapidmicrobiology 2007(Antibiotic Sensitivity Testing—Establishing the MinimumInhibitory Concentration, 1-2).*
McGraw-Hill Encyclopedia of Science and Technology, ISBN 0-07-909206-3, vol. 2, 1992, pp. 525-526.
McGraw-Hill Encyclopedia of Science and Technology, ISBN 0-07-909206-3, vol. 2, 1992, pp. 95-96.

* cited by examiner

*Primary Examiner* — Suzanne Ziska
(74) *Attorney, Agent, or Firm* — Birch, Stewart, Kolasch & Birch, LLP.

(57) ABSTRACT

A use in a medical device of at least one salt of organic acid(s), and preferably a benzoate or a sorbate, as an antimicrobial agent is disclosed, and in particular for the manufacturing of an antimicrobial coating for a medical device, e.g., hydrophyllic urinary catheters, for the prevention of bacterial infection. The pH of the hydrophilic coating may be controlled to be in the range 4.0-8.0, preferably in the range 5.0-6.0, and preferably to be below 7.0. The pH of the hydrophilic coating could be controlled by means of a pH buffer, and preferably a citrate or phosphate buffer. A salt of organic acid in combination with a pH buffer has proven surprisingly efficient for inhibition of bacterial growth, and for prevention of bacterial infections.

28 Claims, 2 Drawing Sheets

CATHETER ASSEMBLY WITH BACTERICIDAL EFFECT

FIELD OF THE INVENTION

The present invention generally relates to the field of bactericidal inhibition, especially for use in medical devices such as urinary catheters

BACKGROUND OF THE INVENTION

Bacterial infections and similar diseases are a common problem related to growth and transfer of microbes in the use of many types of medical devices.

For example, indwelling medical devices such as vascular catheters, peritoneal catheters, cardiovascular devices, orthopedic implants and other prosthetic devices is often offset by infectious complications. The most common organisms causing these infectious complications are *Staphylococcus epidermidis* and *Staphylococcus aureus*. In the case of vascular catheters, these two organisms account for almost 70-80% of all infectious organisms, with *Staphylococcus epidermidis* being the most common organism. *Candida albicans*, a fungal agent, accounts for about 10-15% of catheter infections.

Another common hospital-acquired infection is urinary tract infection (UTI). The majority of cases of UTI are associated with the use of urinary catheters, including hydrophilic catheters with hydrophilic coatings for intermittent use. Each catheter is normally pre-packed in a receptacle by the manufacturer, in order to maintain the catheter in a clean and preferably sterile condition. These urinary catheters are inserted in a variety of populations, including the elderly, stroke victims, spinal cord-injured patients, post-operative patients and those with obstructive uropathy. Despite adherence to sterile guidelines for the insertion and maintenance of urinary catheters, catheter-associated UTI continues to pose a major problem. For instance, it is estimated that almost one-quarter of hospitalized spinal cord-injured patients develop symptomatic UTI during their hospital course. Gram-negative *bacilli* account for almost 60-70%, *enterococci* for about 25% and *Candida* species for about 10% of cases of UTI. When medical devices such as a catheter with a hydrophilic coating is introduced into the human cavity, the normal human defense barrier may be penetrated which can result in introduction of bacteria, fungi, vira, or tissue-like or multiple organized cells. It is well known that persons practicing intermittent urethral catheterization as a daily routine often have problems with symptomatic UTI. Similarly, a number of other medical devices that come in intimate contact with human tissue can cause microbial infections.

Colonization of bacteria on the surfaces of the catheter or other part of the device can produce serious patient problems, including the need to remove and/or replace the implanted device and to vigorously treat secondary infective conditions. A considerable amount of attention and study has been directed toward preventing such colonization by the use of antimicrobial agents, such as antibiotics, bound to the surface of the materials employed in such devices. In such attempts the objective has been to produce a sufficient bacteriostatic or bactericidal action to prevent colonization. For example, methods of coating surfaces of medical devices with antibiotics are taught in U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders). U.S. Pat. No. 4,612,337 discloses an implantable medical device comprising a non-metallic material, and an antimicrobial composition, of an effective concentration to inhibit the growth of bacterial and fungal organisms, coating the surface of the implant and impregnating the non-metallic material of the medical implant.

It is also known to use antimicrobial compounds without antibiotic effects. For example, it is known from EP 1 104 311 to use silver as an antibacterial agent, and it is known from WO 2004/075944 to use hydrogen peroxide to the same end.

However, a problem related to many of the prior art solutions are that they are relatively costly and complex to produce. A further problem is the many negative secondary effects associated with most of the proposed anti-microbial compounds.

There is therefore a need for an antimicrobial compound and coating that can provide high bactericidal efficacy and broad spectrum antimicrobial activity coupled with low cytotoxicity. There is also a need for a cost effective product.

SUMMARY OF THE INVENTION

It is a general object of the present invention to alleviate the above-discussed problems.

One object of the present invention is to provide a use in a medical device of an antimicrobial agent that alleviates at least some of the above-related problems.

Another object of the present invention is to provide a use of an agent for the manufacturing of an antimicrobial coating for a medical device for the prevention of bacterial infection that alleviates at least some of the above-related problems.

Another object of the present invention is to provide a use of an agent as a pharmaceutical that alleviates at least some of the above-related problems.

Another object of the present invention is to provide a method of making a hydrophilic coating of a medical device antimicrobial that alleviates at least some of the above-related problems.

Another object of the present invention is to provide a medical device, a catheter assembly and a wetting fluid that alleviates at least some of the above-related problems.

Another object of the present invention is to provide a method for producing a catheter assembly that alleviates at least some of the above-related problems.

Other general and specific objects of the invention will in part be obvious and will in part appear hereinafter.

These objects are achieved with a catheter assembly, a production method, a wetting fluid, and a method of use according to the appended claims.

According to a first aspect, there is provided a use in a medical device of at least one salt of organic acid(s), and preferably a benzoate or a sorbate, as an antimicrobial agent.

According to a second aspect of the invention, there is provided a use of a salt of organic acid for the manufacturing of an antimicrobial coating for a medical device for the prevention of bacterial infection.

According to a third aspect of the present invention, there is provided a use of a salt of organic acid as a pharmaceutical.

Osmolality increasing compounds has previously been found to improve the water retention and low-friction properties of hydrophilic catheters, as has been disclosed e.g in EP 0 217 771 by the same applicant.

It has now surprisingly been found by the present inventors that some osmolality increasing compounds, viz. salts of organic acids, also are useful as antimicrobial agents, in addition to the previously known advantages of an increased osmolality. In particular, salts of benzoates and sorbates have proven useful to this end, such as sodium benzoate and potassium sorbate. It is also possible to use various combinations of different salts of organic acids. Accordingly, said salts of organic acids are also useful for the manufacture of an antimicrobial coating for a medical device for the prevention of bacterial infection. This is advantageous e.g. for manufacturing antimicrobial coatings of urinary catheters for prevention of bacterial infections, and in particular infection of the urinary tract.

Many different attempts have been made over the years to inhibit bacterial growth on medical devices, with various results. However, the solution provided by the present invention has proven remarkably efficient. The salts of organic acids has an adequate antimicrobial effect, and in addition the same salts could serve other ends, such as increasing the osmolality of a hydrophilic coating, whereby the water retention and low-friction properties of the coating are improved. Hereby, the end product becomes less complicated, and with fewer different added compounds, which in turn makes the production process easier and less costly. Further, a limitation of the total number of different substances in the medical device makes it easier to verify that no harmful or unwanted secondary effects occur, etc.

The concentration of the salt(s) from organic acid(s) is preferably in the range 300-1200 mOsm/dm$^3$, and most preferably in the range 600-900 mOsm/dm$^3$. In particular, these osmolality levels refer to the salt concentration of the medical device, or in a possible coating of said medical device, in a wetted stated, such as in a wetted hydrophilic coating. The lower level is generally set to obtain a certain level of bacterial inhibition. It is also preferred that the concentration of the salt(s) from organic acid(s) exceeds the Minimum Inhibitory Concentration (MIC) for at least one pre-selected type of bacteria, and preferably *Escherichia coli* (*E. coli*) bacteria. The higher level is generally set to avoid unwanted and possibly harmful secondary effects on the patient.

The unit milliosmole (mOsm), i.e. one-thousandth of an osmole, represents the amount of substance that dissolves in a solvent to form one mole of osmotically active units (atoms, ions, etc), e.g., 1 mole of glucose, which is not ionizable, forms 1 osmole of solute, but 1 mole of sodium chloride forms 2 osmoles of solute.

This very high concentration of the salt, exceeding 300 or 600 mOsm/dm$^3$, has proven remarkably efficient with regard to the above-discussed antimicrobial properties, and also in respect of properties related to the increased osmolality, such as increased stability during wetting, and thereby stability during use, low friction, and in particular a lowered extraction force, and improved water retention. Specifically, the high concentration according to the invention is in line with the normal saline concentration in urine (which is about 900 mOsm/dm$^3$) and is much higher than the concentration in a physiological saline solution (about 290 mOsm/dm$^3$). It has surprisingly been found by the present inventors that when a such a high concentration is used for the wetting fluid, the properties of the resulting wetted hydrophilic layer is dramatically improved in respect of. No negative side-effects has been noted by the proposed high concentrations.

The invention is e.g. useful in medical devices having a hydrophilic coating, such hydrophilic urinary catheters. It is then preferred that the pH of the hydrophilic coating is controlled to be in the range 4.0-8.0, and preferably in the range 5.0-6.0. It is also preferred that the pH of the hydrophilic coating is controlled to be below 7.0. The pH of the hydrophilic coating could be controlled by means of a pH buffer, and preferably a citrate or phosphate buffer. In such an embodiment, the pH buffer is preferably provided in an amount sufficient to provide a concentration of the buffer solution in the hydrophilic coating when wetted in the range 5-80 mMolar. The upper pH limit is important in order to obtain full or adequate antimicrobial effect, whereas the lower pH limit is important to control in order not to generate unwanted or harmful secondary effects.

Preferably, the at least one salt of organic acid(s) could be incorporated in a wetting fluid, usable for providing low-friction surface character of a hydrophilic coating of the medical device by treatment with said wetting fluid, for making the hydrophilic coating antimicrobial when activated by said wetting fluid. In such an embodiment, the addition of the salt to the wetting fluid is a relatively simple procedure, whereby the production becomes very expedient and cost effective. Further, by incorporating the salt in the wetting fluid, the resulting dosage of the salt in wetted hydrophilic surface is easy to control and predetermine, and is also relatively unaffected by the duration of the wetting of the hydrophilic coating. However, additionally or alternatively the at least one salt of organic acid could be incorporated in the medical device, and preferably in a hydrophilic coating of the same.

According to a fourth aspect of the present invention, there is provided a method of making a hydrophilic coating of a medical device antimicrobial, comprising the steps:

providing a medical device substrate;

providing a hydrophilic coating on said medical device substrate; and incorporating a salt from organic acid(s), and preferably a benzoate or a sorbate, into the hydrophilic coating for making the hydrophilic coating antimicrobial.

Similar advantages are provided by this aspect as were already discussed in view of the previous aspects. Also, the above-mentioned embodiments regarding e.g. concentration levels, compounds and pH control apply to this fourth aspect as well. Specifically, the provision of the salt of organic acid has proven surprisingly efficient for inhibition of bacterial growth, and for prevention of bacterial infections.

According to a fifth aspect of the present invention, there is provided a catheter assembly comprising a wetting fluid; a catheter having on its surface, on at least an insertable part thereof, a hydrophilic surface layer providing low-friction surface character of the catheter by treatment with said wetting fluid; and a receptacle enclosing at least the insertable part of the catheter; wherein at least one of the wetting fluid and the catheter further comprises at least one salt of organic acid(s), and preferably a benzoate or a sorbate, and a pH buffer, for making the hydrophilic coating antimicrobial when wetted with the wetting fluid.

Similar advantages are provided by this aspect as were already discussed in view of the previous aspects. Also, the above-mentioned embodiments regarding e.g. concentration levels, compounds and pH control apply to this fifth aspect as well. Specifically, the provision of the salt of organic acid in combination with a pH buffer has proven surprisingly efficient for inhibition of bacterial growth, and for prevention of bacterial infections.

The wetting fluid may be arranged in wetting contact with the hydrophilic surface layer or coating of the catheter in the receptacle, for preservation of the hydrophilic surface layer in a wetted state during accommodation in said receptacle, whereby a ready-to-use catheter assembly is provided. The assembly may also be such that the wetting fluid is initially kept separated from the hydrophilic surface layer of the catheter during storage of the assembly, and brought into contact with the hydrophilic surface layer upon activation before an intended use of the catheter.

The salt of organic acid(s) may be arranged in the catheter or in the wetting fluid, or even in both, and the same applies for the pH buffer.

According to a sixth aspect of the present invention, there is provided a medical device having on at least a part of its surface a hydrophilic surface layer for producing a low-friction surface character of the surface by treatment with a wetting fluid, wherein the hydrophilic coating comprises at least one salt of organic acid(s), and preferably a benzoate or a sorbate, and a pH buffer, for making the hydrophilic coating antimicrobial when wetted with the wetting fluid. The medical device is e.g. a urinary catheter, and preferably a urinary catheter intended for intermittent use.

Similar advantages are provided by this aspect as were already discussed in view of the previous aspects. Also, the above-mentioned embodiments regarding e.g. concentration levels, compounds and pH control apply to this sixth aspect as well. Specifically, the provision of the salt of organic acid in combination with a pH buffer has proven surprisingly efficient for inhibition of bacterial growth, and for prevention of bacterial infections.

According to a seventh aspect of the present invention, there is provided a wetting fluid for activation of a hydrophilic surface layer in order to produce a low-friction surface character of said hydrophilic surface layer by treatment by said the wetting fluid, wherein the wetting fluid comprises at least one dissolved salt of organic acid(s), and preferably a benzoate or a sorbate, and a pH buffer, for making the hydrophilic coating antimicrobial when wetted with the wetting fluid. Preferably, the wetting fluid is a water-based liquid.

Similar advantages are provided by this aspect as were already discussed in view of the previous aspects. Also, the above-mentioned embodiments regarding e.g. concentration levels, compounds and pH control apply to this seventh aspect as well. Specifically, the provision of the salt of organic acid in combination with a pH buffer has proven surprisingly efficient for inhibition of bacterial growth, and for prevention of bacterial infections.

According to a eighth aspect of the present invention, there is provided a method for producing a catheter assembly, comprising:
  providing a receptacle;
  providing a hydrophilic catheter;
  providing a wetting fluid;
  arranging at least an insertable part of the catheter in the receptacle and arranging said wetting fluid as a part of said catheter assembly;
  wherein at least one of the wetting fluid and the catheter further comprises at least one salt of organic acid(s), and preferably a benzoate or a sorbate, and a pH buffer, for making the hydrophilic coating antimicrobial when wetted with the wetting fluid.

Similar advantages are provided by this aspect as were already discussed in view of the previous aspects. Also, the above-mentioned embodiments regarding e.g. concentration levels, compounds and pH control apply to this eighth aspect as well. Specifically, the provision of the salt of organic acid in combination with a pH buffer has proven surprisingly efficient for inhibition of bacterial growth, and for prevention of bacterial infections.

These and other aspects of the inventive concept will be apparent from and elicited with reference to the embodiments described hereinafter.

BRIEF DESCRIPTION OF THE DRAWINGS

By way of example embodiments of the invention will now be described with reference to the accompanying drawings in which.

DESCRIPTION OF PREFERRED EMBODIMENTS

Figure 1:
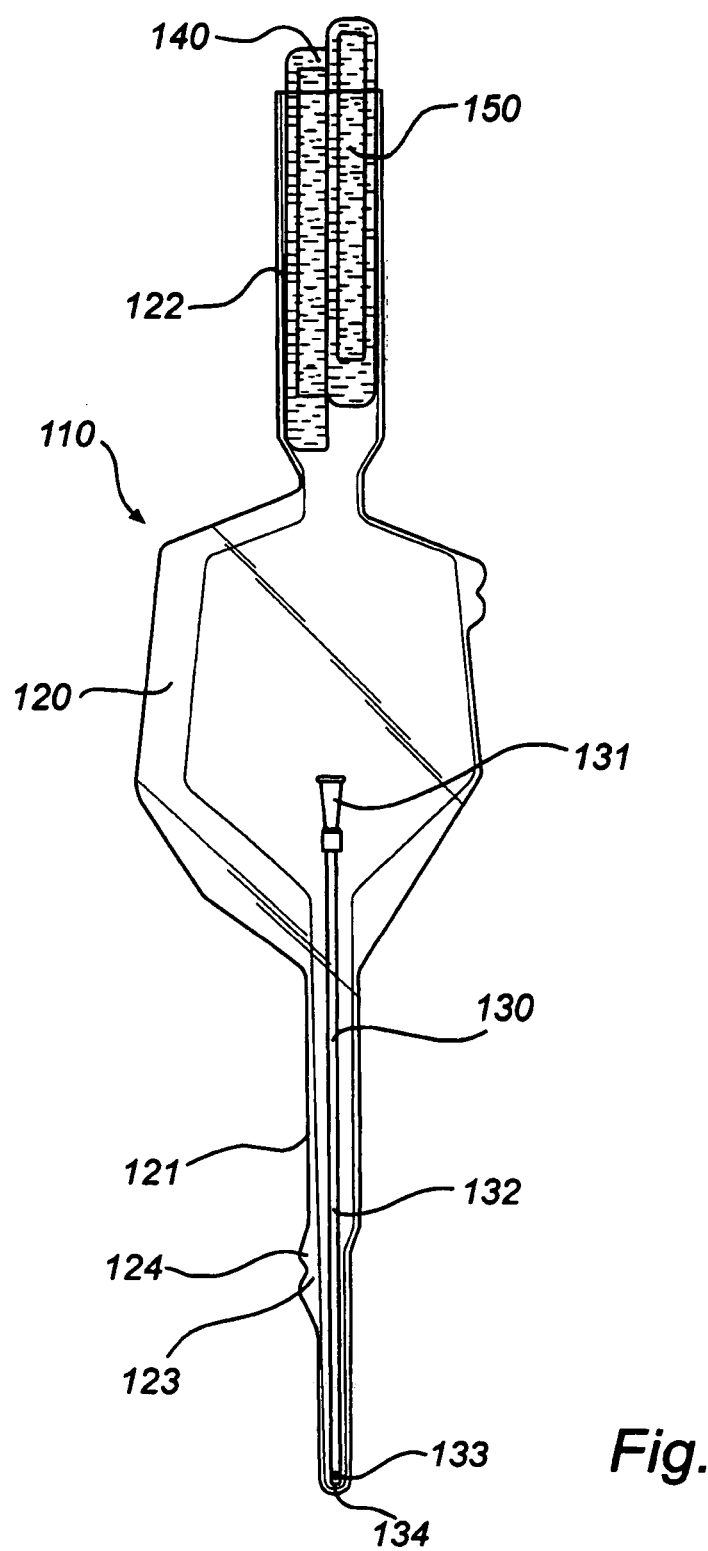
FIG. 1 illustrates an embodiment of a catheter assembly according to the invention, presenting a separately enclosed wetting fluid, said embodiment in structure resembling a catheter assembly disclosed in WO 97/26937.

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter, the dimensions of the fluid compartments, etc.

It is further to be appreciated by those skilled in the art that even though all the embodiments are related to urinary catheters, the inventive concept is not limited to this type of devices, but could also be used in many other types of medical devices.

The present inventors have surprisingly found that salts of organic acids has an adequate antimicrobial effect for use as antimicrobial agents in medical devices such as hydrophilic catheters. In particular, salts of benzoates and sorbates have proven useful to this end, such as sodium benzoate and potassium sorbate. It is also possible to use various combinations of different salts of organic acids.

The concentration of the salt(s) from organic acid(s) is preferably in the range 300-1200 $mOsm/dm^3$, and most preferably in the range 600-900 $mOsm/dm^3$. The lower level is generally set to obtain a certain level of bacterial inhibition. It is also preferred that the concentration of the salt(s) from organic acid(s) exceeds the Minimum Inhibitory Concentration (MIC) for at least one pre-selected type of bacteria, such as *E. coli* bacteria. The higher level is generally set to avoid unwanted and possibly harmful secondary effects on the patient.

The at least one salt of organic acid(s) could be used in the medical devices in different ways, such as:
  It could be dissolved in a wetting fluid, usable for providing low-friction surface character of a hydrophilic coating of the medical device by treatment with said wetting fluid, for making the hydrophilic coating antimicrobial when activated by said wetting fluid.
  It could be incorporated in a surface coating of the medical device, such as in a hydrophilic surface coating of a urinary catheter. Such incorporation into the coating could e.g. be accomplished by the method discussed in EP 0 217 771 by the same applicant.

It could be incorporated in both the surface coating and a wetting fluid for activation of said coating.

The invention is e.g. useful in medical devices having a hydrophilic coating, such hydrophilic urinary catheters. It is then preferred that the pH of the hydrophilic coating is controlled to be in the range 4.0-8.0, and preferably in the range 5.0-6.0. It is also preferred that the pH of the hydrophilic coating is controlled to be below 7.0. The pH of the hydrophilic coating could be controlled by means of a pH buffer, and preferably a citric acid buffer. In such an embodiment, the pH buffer is preferably provided in an amount sufficient to provide a concentration of the buffer solution in the hydrophilic coating when wetted in the range 5-80 mMolar. The upper pH limit is important in order to obtain full or adequate antimicrobial effect, whereas the lower pH limit is important to control in order not to generate unwanted or harmful secondary effects. The pH buffer could be a phosphate, comprising e.g. sodium or potassium phosphate salts.

In a preferred embodiment, the organic acid is used in a catheter having a hydrophilic outer surface coating. Hydrophilic catheters may be used for many different purposes, and for insertion into various types of body-cavities. However, the following discussion is in particular concerned with the preferred field of use, urinary catheters, even though the invention is not limited to this particular type of catheters.

A catheter 130 as illustrated in the drawings, e.g. in FIG. 1, comprises a flared rearward portion 131 and an elongate shaft or tube 132 projecting forwardly from the rearward portion 131. An open-ended internal lumen (not shown) extends from the rear end of the rearward portion 131 to a drainage aperture 133 in a rounded tip 134 of the elongate tube 132. The rearward portion 131 may function as a connector of the catheter 130, being connectable to other devices, such as a urine collection bag, a drainage tube or the like.

At least a part of the elongate tube 132 forms an insertable length to be inserted through a body opening of the user, such as the urethra in case of a urinary catheter. By insertable length is normally, in the context of a hydrophilic catheter, meant that length of the elongate tube 132 which is coated with a hydrophilic material, for example PVP, and which is insertable into the urethra of the patient. Typically, this will be 80-140 mm for a female patient and 200-350 mm for a male patient.

According to the invention, and applicable for the embodiments disclosed herein, the wetting fluid may be used for the wetting of many different types of well-known hydrophilic surfaces. For example, the catheter may be provided with a hydrophilic coating wherein the hydrophilic polymer coating comprises material selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone.

The catheter may be arranged separately in a package. However, preferably the catheter is arranged in assembly additionally comprising a wetting fluid. With reference to FIG. 1, a first embodiment of a catheter assembly will now be described, the structure of which generally resemblings embodiments previously disclosed in WO 97/26937, hereby incorporated by reference.

The catheter assembly 110 comprises a wetting receptacle or bag 120, preferably of a transparent flexible plastics material. The receptacle 120 has an elongate pocket 121 at its forward end. At its rearward end 122 the receptacle presents an opening. The wetting receptacle 120 is adapted for accommodation of at least the insertable length of the catheter tube 132 in the elongate pocket 121.

The catheter assembly 110 further comprises a hydrophilic urinary catheter 130, as is discussed in more detail in the foregoing.

The catheter assembly 110 comprises a wetting fluid 150 forming part of the assembly 110, i.e. the wetting fluid is not provided completely separate from the assembly. More specifically, in the embodiment in FIG. 1, the catheter assembly 110 further comprises a wetting fluid container 140, in which the wetting fluid 150 is kept separated from the hydrophilic surface of the catheter 130 during storage.

The wetting fluid container 140 is openable, in order to enable activation of the catheter assembly. Thus, the activation is performed by opening the container and releasing the wetting fluid into the wetting receptacle 120 so that it comes into contact with the hydrophilic coating of the catheter 130. The wetting fluid container 140 may be openable by means of pressing, tearing, piercing, twisting, etc, which is per se well-known in the art. The wetting fluid 150 is discussed in more detail in the foregoing.

The wetting receptacle 120 preferably forms a sealed compartment around the catheter 3 and at least part of the wetting fluid container 140.

The wetting receptacle 120 preferably comprises opening means for facilitating opening of the receptacle in order to expose the catheter 130 for use. The opening means may comprise a tear line 123 connected to a gripping handle 124, such as a pulling tab. Hereby, the user may pull the gripping handle 124 and, thereby, tearing open the side wall of the wetting receptacle 120. Additionally, or alternatively, a gripping handle may be arranged in the opposite end of the tear line 123. However, alternative opening means are also feasible, such as tear-lines arranged in different fashions and locations, peel-off joints, etc.

In a method of wetting the catheter 130 according to the embodiment in FIG. 1, the user first activates the catheter 130 by opening the wetting fluid container 140 within the bounds of the wetting receptacle 120, thereby releasing the wetting fluid from the container 140 into the wetting receptacle 130. After a sufficient wetting period, the wetting receptacle 120 is opened, in order to expose the catheter 130 for insertion into a patient.

Figure 2:
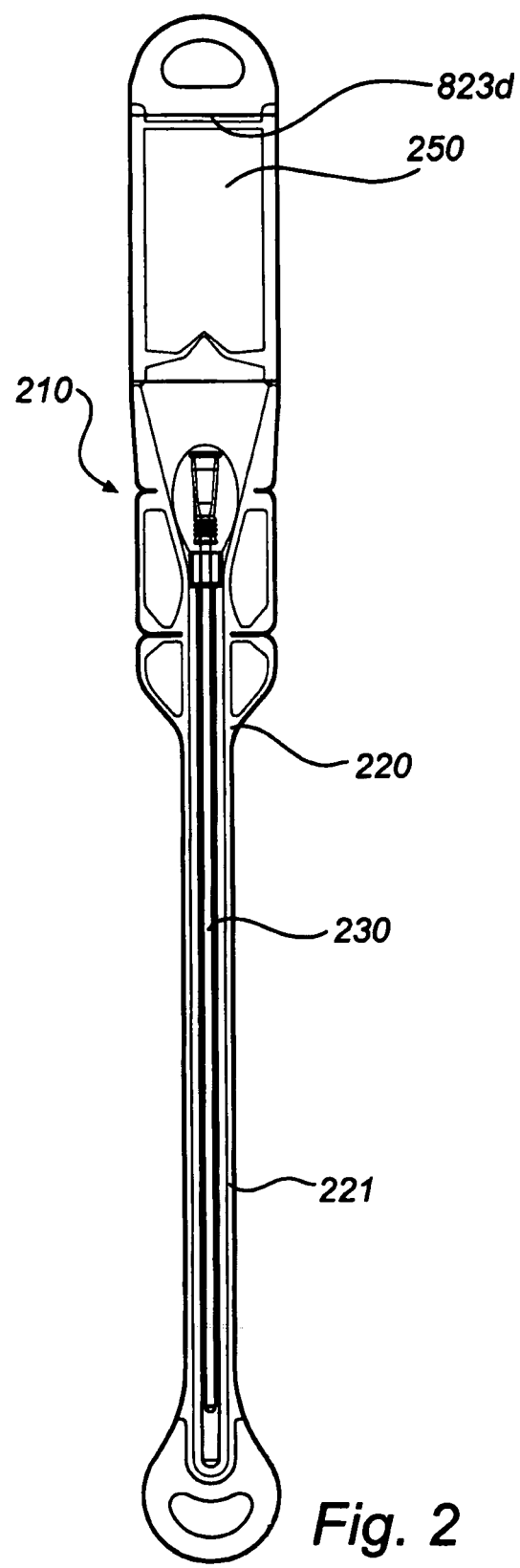
FIG. 2 is a partly broken side view of another embodiment embodiment of a catheter assembly according to the invention, also presenting a separately enclosed wetting fluid, said embodiment in structure resembling another catheter assembly disclosed in WO 03/092779.

In the embodiment in FIG. 1, the wetting receptacle 120 also serves as a urine collection bag. Thus, being opened, the receptacle 120 maintains connected to the catheter 120 for receiving the drained urine from the bladder. However, this is merely optional, and a package not serving as a urine collection bag is equally feasible. Such an embodiment is illustrated in FIG. 2, which resembles the structure of some embodiments discussed in WO 03/092779, which are hereby incorporated by reference. With reference to WO 03/092779, element 823d is a peelable joint, and element 250 is a wetting fluid container. Analogously to similar elements shown in FIG. 1 of this Application, element 210 is a catheter assembly, element 220 is the wetting receptacle, element 230 is the catheter bore, element 232 is the catheter tube, and element 221 is an elongate pocket.

Alternatively, the catheter assembly may comprise a package only partly enclosing the catheter, as is also disclosed in WO 03/092779, hereby incorporated by reference. It is also possible to arrange the wetting fluid container not in a separate compartment of the receptacle, but integrated with the compartment holding the catheter. Hereby, the catheter is activated already during production, and is then maintained in a activated, ready-to-use condition. Thus, in this embodiment, the hydrophilic surface layer is preserved in a wetted state during accommodation in the receptacle and a ready-to-use catheter assembly is provided. In order to preserve this wetted condition the compartment formed by the receptacle and the catheter is preferably gas sealed, and further, the receptacle is preferably gas impermeable. In use, the receptacle is simply opened, and the catheter could immediately be introduced into the patient. Such an assembly is e.g. disclosed in WO 00/47494, hereby incorporated by reference.

The wetting fluid serves the primary purposes of wetting the hydrophilic surface coating, whereby a low-friction character of the surface is produced. However, as previously discussed, it is also possible to provide a dissolved antimicrobial compound in the fluid. The wetting fluid is preferably a water-based liquid, i.e. using water as a solvent. Still further, the wetting fluid could also comprises a dissolved hydrophilic polymer, and preferably the same hydrophilic polymer as in the hydrophilic coating of the catheter for which the wetting fluid is intended. The amount of hydrophilic polymer in the wetting fluid is preferably in the range 0-20% of weight, and most preferably in the range 5-15%, and typically about 10%.

The salt of organic acid, such as salts of benzoates and sorbates, could in the exemplary embodiments above be incorporated into both the wetting fluid and into the hydrophilic coating of the catheter, wherein the concentrations in the wetting fluid and in the hydrophilic coating, respectively, are high enough to provide a total dissolved concentration in the hydrophilic coating when wetted in preparation for an intended use. However, it is also possible to incorporate the salts solely in the hydrophilic coating before the wetting, or solely in the wetting fluid, and in a concentration high enough to provide the intended dissolved concentration when wetted in preparation for an intended use. For incorporation of the salts into the coating, any one of the per se known methods discussed in the background section may be used, such as e.g. the method disclosed in EP 217 771.

The substrates may be made from any polymer material, which are well-known in the technical field and to which the said hydrophilic polymers adhere, such as polyurethanes, latex rubbers, other rubbers, polyvinylchloride, other vinyl polymers, polyesters and polyacrylates.

EXPERIMENTS

Experimental tests were conducted in order to verify the above-discussed results. In the experiments, solutions were prepared and sterilized by radiation (E-beam) or heat (autoclave). In some of the solutions Sodium Benzoate (NaB) and/or Potassium Sorbate (KS) was dissolved. All the solutions were then adjusted for osmolality by adding sodium chloride (NaCl) to the solution. NaCl was added so that a target value of about 900 mOsm was reached for all the solutions. Further, some of the solutions were buffered to a predetermined pH-value with a citrate buffer (a buffer-system consisting of sodium citrates).

All solutions were mixed with three volumetric parts synthetic urine in the experiments. Synthetic urine supports bacterial growth and were used as growth medium as well as negative control reference in the experiments.

All experiments were made on the bacteria *Escherichia coli*, since the *E. coli* bacteria is normally the most relevant bacteria to inhibit for urinary catheter products.

MIC (Minimum Inhibitory Concentration) tests were performed to assess the potential of a given substance and concentration to inhibit bacterial growth. The solutions were added to a growth solution containing a specified number of bacteria. The bacteria were then grown in microtiter-wells at 37 deg. C. in a Bioscreen-instrument for a period of at least 40 hours. The bacterial growth/inhibition was monitored in terms of optical density for the solution. Since all microorganisms increase the optical density of a solution during growth and multiplication, the Bioscreen measure of the transmittance/absorbance of light through the sample is correlated to the concentration of microorganisms.

The results of the measurements of the different solutions are compared to a negative control reference, i.e. to synthetic urine, for each set of experiments. The actual inhibition times are not shown, but instead an index value corresponding to the relative effectiveness in prolonging the inhibition time compared to synthetic urine is displayed for each substance. For example, if synthetic urine had bacterial growth after 5 hours and "substance A" had bacterial growth after 10 hours, the resulting index value for "substance A" would be 2 (10/5=2 times as effective as synthetic urine). An index value of ">8" corresponds to no growth at all of the bacteria during the course of the experiment.

TABLE 1

Measurement of bacterial growth inhibition for different solutions.

| No | Substance | Concentration (w/w)* | Osmolality (mOsm)* | pH* | Buffering substance | Result (index) |
|----|-----------|----------------------|--------------------|-----|----------------------|----------------|
| 1  | NaCl      | 3.0%                 | 1700               | 6.5 | —                    | 1.5            |
| 2  | NaCl      | 0.9%                 | 900                | 6.5 | —                    | 1.0            |
| 3  | NaB       | 1.0%                 | 850                | 6.5 | —                    | 5.3            |
| 4  | NaB       | 0.3%                 | 850                | 6.5 | —                    | 4.0            |
| 5  | NaB       | 0.1%                 | 850                | 6.5 | —                    | 2.3            |
| 6  | NaB       | 0.25%                | 860                | 5.0 | Citrate              | >8.0           |
| 7  | NaB       | 0.25%                | 860                | 5.6 | Citrate              | >8.0           |
| 8  | NaB       | 0.25%                | 860                | 5.9 | Citrate              | >8.0           |
| 9  | NaB       | 0.25%                | 860                | 6.5 | —                    | 4.0            |
| 10 | KS        | 1.0%                 | 850                | 6.5 | —                    | 5.3            |
| 11 | KS        | 0.3%                 | 850                | 6.5 | —                    | 5.0            |
| 12 | KS        | 0.1%                 | 850                | 6.5 | —                    | 3.8            |
| 13 | KS        | 0.05%                | 870                | 5.0 | Citrate              | >8.0           |
| 14 | KS        | 0.05%                | 860                | 5.6 | Citrate              | 1.8            |
| 15 | KS        | 0.05%                | 860                | 5.9 | Citrate              | 1.7            |
| 16 | KS        | 0.05%                | 860                | 6.5 | —                    | 1.2            |
| 17 | NaB + KS  | 0.5 + 0.5%           | 850                | 6.5 | —                    | 5.3            |
| 18 | NaB + KS  | 0.15 + 0.15%         | 850                | 6.5 | —                    | 4.3            |
| 19 | NaB + KS  | 0.05 + 0.05%         | 850                | 6.5 | —                    | 2.5            |
| 20 | NaB + KS  | 0.125 + 0.025%       | 860                | 5.0 | Citrate              | >8.0           |
| 21 | (control) | —                    | 860                | 5.0 | Citrate              | 2.0            |
| 22 | (control) | —                    | 860                | 5.6 | Citrate              | 1.2            |
| 23 | (control) | —                    | 860                | 5.9 | Citrate              | 1.2            |

*= approximate value after mixing 1 + 3 with synthetic urine in the experiments.

Several conclusions are derivable from the above-presented measurements. For example, it can be seen that the addition of salt(s) from organic acids (NaB and/or KS) significantly inhibits the bacterial growth in the solution compared to solutions (No 1 and 2) only comprising NaCl as the osmolality increasing compound and the control solutions (No 21-23).

From measurements No 3-5, 10-12 and 17-19 it can be concluded that the inhibition of bacterial growth is improved when the concentration (w/w) of the salt(s) of organic acid is above 0.3%, and even more improved when the concentration exceeds 1.0%. This dramatic improvement is surprising, since only a very limited increase is seen in measurements No 1 and 2, where the concentration of NaCl is increased from 0.9% to 3.0%.

From measurements No 6-9, 13-16 and 20, it can be concluded that the bacterial growth inhibition is dramatically improved when the pH is controlled to be below 6.5, and specifically in the range 5-6. As is illustrated by the control measurements No 21-23, these effects are not achieved by the decreased pH in itself, but is due to the synergy with the salt(s) of organic acid. As is particularly obvious from the measurements No 13-16, this synergy effect is significant even when very low concentrations of the organic acid salt is used. From said measurements it is also obvious that the bacterial growth inhibition is significantly improved when lowering the pH below 6, and that dramatic improvements are achieved in the vicinity of pH 5.

CONCLUSION AND SUMMARY

The invention has now been discussed in relation to different embodiments. However, it should be appreciated by those versed in the art that several further alternatives are possible. For example, the features of the different embodiments discussed above may naturally be combined in many other ways.

It is further possible to use the invention for other types of catheters than urinary catheters, such as vascular catheters or the like. It is also possible to use many different types of salts of organic acid(s), either alone or in different combinations. Many different levels of concentration of the salts are also feasible, even though the higher levels proposed in the foregoing are normally more advantageous.

Still further, in the assemblies comprising a wetting fluid container, it is possible to arrange the wetting fluid container in many different ways. For example, the container may be a separate container, but forming part of the assembly. Such a wetting fluid container may be arranged completely inside the receptacle, partly inside the receptacle, or completely outside the receptacle. Alternatively, the wetting fluid container may be an integrated compartment of the receptacle. This compartment may be separated from the compartment housing the insertable part of the catheter, or be integrated with such a compartment. In the latter case, the catheter may be maintained in a wetted, activated state.

Further, the wetting fluid container may be arranged close to the distal part of the catheter, close to the proximal part of the catheter, or in any other suitable location in the assembly. In case the wetting fluid is arranged separately from the insertable part of the catheter, the separation wall or joint could e.g. be a breakable or peelable membrane wall, but alternative embodiments are naturally feasible, such as various types of detachable or openable caps or closings. The wetting fluid container may be arranged to be discharged upon application of a twist, a compression, a pull or the like on the fluid container. Preferably the wetting fluid may be discharged without breaking or rupturing the receptacle, even though this may not be necessary, depending on the intended use, etc.

Many different materials could also be used for the different parts of the catheter assembly.

It will be appreciated by those versed in the art that several such alternatives similar to those described above could be used without departing from the spirit of the invention, and all such modifications should be regarded as a part of the present invention, as defined in the appended claims.

The invention claimed is:

1. A method of making a urinary catheter, comprising;
    providing a urinary catheter with a hydrophilic coating;
    providing the urinary catheter with an antimicrobial agent which contains at least one salt of organic acid(s), said salt of organic acid(s) being at least one of sodium benzoate and potassium sorbate, wherein the concentration of the salt(s) from organic acid(s) is in the range of 600-900 mOsm/dm$^3$ in the hydrophilic coating when it is wetted; and
    controlling the pH of the hydrophilic coating to be in a range of 5.0-6.0.

2. A method of using the urinary catheter of claim 1, comprising:
    using the urinary catheter in a human for the prevention of bacterial infection.

3. The method of claim 1, wherein the concentration of the salt(s) from organic acid(s) exceeds the Minimum Inhibitory Concentration (MIC) for at least *Escherichia coli* (*E. coli*).

4. The method of claim 1, further comprising providing a citrate or phosphate pH buffer for controlling the pH of the hydrophilic coating.

5. The method of claim 4, wherein the pH buffer is provided in an amount sufficient to provide a concentration of the buffer solution in the hydrophilic coating when wetted in the range 5-80 mMolar.

6. A method of making a hydrophilic coating of a urinary catheter antimicrobial, comprising the steps:
    providing a urinary catheter substrate;
    providing a hydrophilic coating on said urinary catheter substrate; and
    incorporating a salt of organic acids of a benzoate or a sorbate, said salt of organic acid(s) being one or more of sodium benzoate and potassium sorbate, wherein the concentration of the salt(s) from organic acid(s) in in the range 600-900 mOsm/dm$^3$ in the hydrophilic coating when it is wetted, and
    controlling the pH of the hydrophilic coating to be in a range of 5.0-6.0 for making the hydrophilic coating antimicrobial.

7. A urinary catheter assembly comprising:
    a wetting fluid;
    a urinary catheter having on its surface, on at least an insertable part thereof, a hydrophilic surface layer providing low-friction surface character of the catheter by treatment with said wetting fluid; and
    a receptacle enclosing at least the insertable part of the catheter;
    wherein the wetting fluid further comprises at least one salt of organic acid(s) of a benzoate or a sorbate, at least one second salt, and a pH buffer, for making the hydrophilic coating antimicrobial when wetted with the wetting fluid,
    wherein the salt of organic acid(s) and the second salt are provided in an amount sufficient to make the concentration of the salt in the hydrophilic coating when wetted to be in the range 600-900 mOsm/dm$^3$,
    wherein the concentration of the salt of organic acid(s) is above 0.3% (w/w), and
    wherein the pH buffer stabilizes the pH in the hydrophilic coating when wetted to a value in the range 4.0-8.0.

8. The urinary catheter assembly of claim 7, wherein the pH buffer is a citrate buffer.

9. The urinary catheter assembly of claim 7, wherein the pH buffer is provided in an amount sufficient to provide a concentration of the buffer solution in the hydrophilic coating when wetted in the range 5-80 mMolar.

10. The urinary catheter assembly as claimed in claim 7, wherein the wetting fluid is arranged in wetting contact with the hydrophilic surface layer of the catheter in the receptacle, for preservation of the hydrophilic surface layer in a wetted state during accommodation in said receptacle and provision of a ready-to-use catheter assembly.

11. The urinary catheter assembly as claimed in claim 7, wherein said assembly presents a storage state in which the wetting fluid is kept separated from the hydrophilic surface layer of the catheter, and an activation state in which the wetting fluid is brought into contact with said hydrophilic surface layer before an intended use of the catheter.

12. A urinary catheter having on at least a part of its surface a hydrophilic surface layer for producing a low-friction surface character of the surface by treatment with a wetting fluid, wherein the hydrophilic coating comprises at least one salt of organic acid(s), said at least one salt of organic acid(s) being potassium sorbate, and a pH buffer, for making the hydrophilic coating antimicrobial when wetted with the wetting fluid.

13. The urinary catheter of claim 12, wherein the pH buffer is a phosphate, comprising e.g. sodium or potassium, or a citrate buffer.

14. The urinary catheter of claim 12, wherein the pH buffer is provided in an amount sufficient to provide a concentration of the buffer solution in the hydrophilic coating when wetted in the range 5-80 mMolar.

15. The urinary catheter as claimed in claim 12, wherein the medical device is a urinary catheter adapted to be used intermittently.

16. A wetting fluid adapted to activate a hydrophilic surface layer of a urinary catheter device in order to produce a low-friction surface character of said hydrophilic surface layer by treatment by said wetting fluid,
wherein the wetting fluid comprises at least one dissolved salt of organic acid(s) of a benzoate or a sorbate, and at least one additional salt, the salts being provided in an amount sufficient to make the concentration of the salt in the hydrophilic surface layer when wetted to be in the range 600-900 mOsm/dm$^3$, and a pH buffer adapted to stabilize the pH in the hydrophilic surface when wetted to a value in the range 4.0-8.0, wherein the concentration of the salt of organic acid(s) is above 0.3% (w/w), and wherein the hydrophilic coating becomes antimicrobial when wetted with the wetting fluid.

17. The wetting fluid of claim 16, wherein the pH buffer is a phosphate, comprising a citrate buffer.

18. The wetting fluid of claim 16, wherein the pH buffer is provided in an amount sufficient to provide a concentration of the buffer solution in the hydrophilic coating when wetted in the range 5-80 mMolar.

19. The wetting fluid of claim 16, wherein the wetting fluid is a water-based liquid.

20. A method for producing a urinary catheter assembly, comprising: providing a receptacle;
providing a hydrophilic urinary catheter;
providing a wetting fluid;
arranging at least an insertable part of the urinary catheter in the receptacle and arranging said wetting fluid as a part of said catheter assembly;
wherein at least one of the wetting fluid and the catheter further comprises at least one salt of organic acid(s) of a benzoate or a sorbate, the concentration of said salt of organic acid(s) exceeding 0.3% (w/w), and wherein the concentration of salt(s) being sufficient to make the concentration of salt(s) in the hydrophilic urinary catheter when wetted to be in the range 600-900 mOsm/dm$^3$, and a pH buffer which stabilizes the pH in the hydrophilic catheter when wetted to a value in the range 4.0-8.0, and wherein the hydrophilic catheter becomes antimicrobial when wetted with the wetting fluid.

21. The urinary catheter assembly as claimed in claim 7, wherein the concentration of the salt of organic acid(s) of a benzoate or a sorbate exceeds the Minimum Inhibitory Concentration (MIC) for at least *Escherichia coli* (*E. coli*).

22. A urinary catheter assembly comprising:
a wetting fluid;
a urinary catheter having on its surface, on at least an insertable part thereof, a hydrophilic surface layer providing low-friction surface character of the catheter by treatment with said wetting fluid; and
a receptacle enclosing at least the insertable part of the catheter,
wherein at least one of the wetting fluid and the catheter further comprises at least one antimicrobial salt of organic acid(s) of a benzoate or a sorbate, the concentration of said salt of organic acid(s) being in a range of 0.05-0.25% (w/w), and a pH buffer, for making the hydrophilic coating antimicrobial when wetted with the wetting fluid,
wherein the concentration of salt(s) is sufficient to make the concentration of the salt(s) in the hydrophilic coating when wetted to be in the range 600-900 mOsm/dm$^3$,
wherein the concentration of the salt of organic acid(s) of a benzoate or a sorbate exceeds the Minimum Inhibitory Concentration (MIC) for at least *Escherichia coli* (*E. coli*) and
wherein the pH buffer is arranged to stabilize the pH in the hydrophilic coating when wetted to a value in a range of 5.0-6.0.

23. A urinary catheter assembly comprising:
a wetting fluid;
a urinary catheter having on its surface, on at least an insertable part thereof, a hydrophilic surface layer providing low-friction surface character of the urinary catheter by treatment with said wetting fluid; and
a receptacle enclosing at least the insertable part of the urinary catheter,
wherein at least one of the wetting fluid and the urinary catheter further comprises at least one antimicrobial salt of organic acid(s) of a sorbate in an amount sufficient to make the concentration of the salt in the hydrophilic surface layer when wetted to be in the range 600-900 mOsm/dm$^3$, and a pH buffer which stabilizes the pH in the hydrophilic surface layer when wetted to a value in the range 4.0-8.0, for making the hydrophilic coating antimicrobial when wetted with the wetting fluid.

24. The urinary catheter assembly of claim 7, wherein the second salt is sodium chloride.

25. The urinary catheter assembly of claim 7, wherein the pH buffer stabilizes the pH in the hydrophilic coating when wetted to a value in the range 5.0-6.0.

26. The urinary catheter of claim 12, wherein the concentration of the potassium sorbate is above 0.3% (w/w).

27. The wetting fluid urinary of claim 16, wherein the second salt is sodium chloride.

28. The wetting fluid of claim 16, wherein the pH buffer stabilizes the pH in the hydrophilic coating when wetted to a value in the range 5.0-6.0.

* * * * *